(12) United States Patent
Linderman et al.

(10) Patent No.: US 9,307,961 B2
(45) Date of Patent: Apr. 12, 2016

(54) FINE NEEDLE ASPIRATION BIOPSY DEVICE

(75) Inventors: Evan Linderman, Deerfield, IL (US);
John Krueger, Muskego, WI (US);
Michael Plishka, Lake Villa, IL (US)

(73) Assignee: CAREFUSION 2200, INC., San Diego, CA (US)

( * ) Notice: Subject to any disclaimer, the term of this patent is extended or adjusted under 35 U.S.C. 154(b) by 56 days.

(21) Appl. No.: 13/538,485

(22) Filed: Jun. 29, 2012

(65) Prior Publication Data

US 2014/0005570 A1    Jan. 2, 2014

(51) Int. Cl.
*A61B 10/00*    (2006.01)
*A61B 10/02*    (2006.01)

(52) U.S. Cl.
CPC .......... *A61B 10/0283* (2013.01); *A61B 10/0275* (2013.01); *A61B 2010/0208* (2013.01)

(58) Field of Classification Search
CPC .................... A61B 10/0283; A61B 2010/0208
USPC .......... 600/562, 565, 571; 604/118, 173, 319; 606/167
See application file for complete search history.

(56) References Cited

U.S. PATENT DOCUMENTS

| | | | | |
|---|---|---|---|---|
| 5,012,818 | A * | 5/1991 | Joishy ........................... | 600/567 |
| 6,193,672 | B1 * | 2/2001 | Clement ................ | A61B 18/14 |
| | | | | 600/565 |
| 7,351,210 | B2 * | 4/2008 | Cicenas et al. ................ | 600/564 |
| 7,462,181 | B2 * | 12/2008 | Kraft .................... | A61B 10/025 |
| | | | | 606/108 |
| 7,670,299 | B2 * | 3/2010 | Beckman et al. ............. | 600/566 |
| 7,881,427 | B2 * | 2/2011 | Kalender ............. | A61B 5/4312 |
| | | | | 378/37 |
| 2007/0106176 | A1 * | 5/2007 | Mark et al. ..................... | 600/566 |
| 2008/0243028 | A1 * | 10/2008 | Howard et al. ................ | 600/565 |

* cited by examiner

*Primary Examiner* — Devin Henson
(74) *Attorney, Agent, or Firm* — Arent Fox LLP

(57) ABSTRACT

A fine needle aspiration device with a modified handle and cannula through which a vacuum is delivered to the targeted tissue for removal of liquid or cellular samples is provided, the vacuum being provided via a flexible tubing capable of fitting within a restricted space such as, for example, a CT gantry. A vacuum source may be provided to assist the fine needle aspiration procedure via flexible tubing, which allows the vacuum source to be located outside the CT gantry or on the patient.

18 Claims, 5 Drawing Sheets

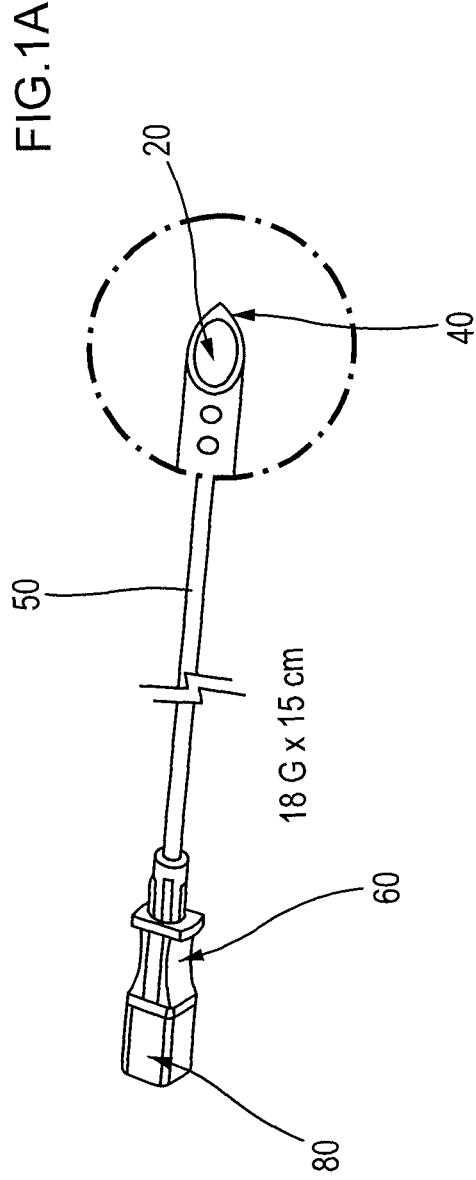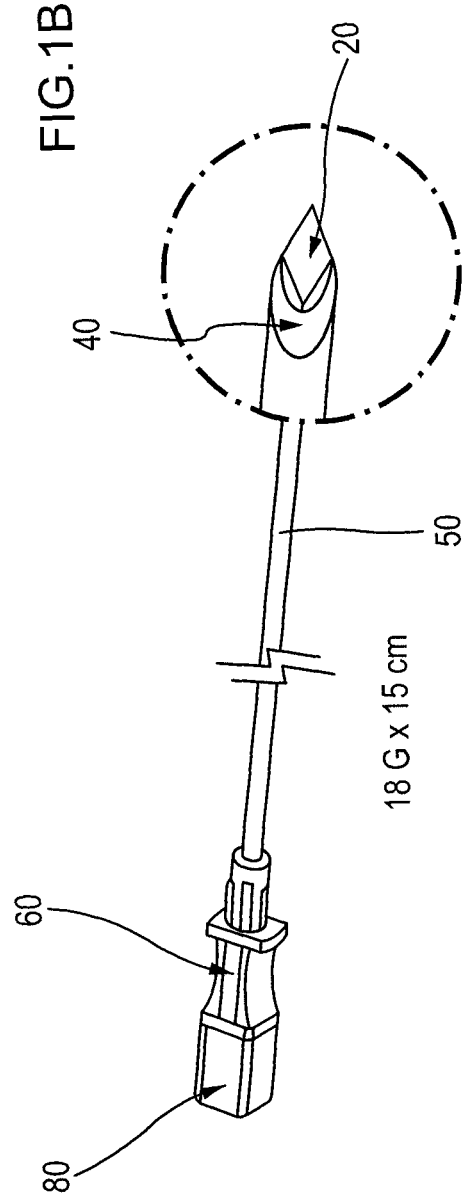

FINE NEEDLE ASPIRATION BIOPSY DEVICE

BACKGROUND OF THE INVENTION

1. Field of Invention

Aspects of the present invention relate to methods and devices for performing biopsy assisted with an aspiration device. More particularly, aspects of the current invention relate to methods and devices for performing biopsy with a fine needle aspiration device usable in a confined space.

2. Description of Related Art

Biopsy devices for fine needle aspiration, such as the one illustrated in FIGS. 1A-1B, are well known in the art and are useful for obtaining cytologic specimens for examination, for example, to confirm the diagnosis of a suspected medical condition. Typical specimens collected include liquids or cell samples. Such devices are generally useful in sampling tissue from the breast, the head and neck, lymph nodes, and for some gynecologic conditions. Other applications include lung, prostate, and other soft tissue biopsies.

Generally, biopsy instruments of this type extract samples of tissue through a small needle in the range of 25-18 gauge. The needle is inserted, typically through the skin, so that the tip of the needle is in the suspect tissue. A vacuum force is sometimes applied by withdrawing the plunger of a standard syringe attached to the needle, while the needle is slightly moved a plurality of times in the tissue, utilizing an up-and-down motion. This procedure draws up a small amount of tissue fluid, together with loose cells, into the needle with some concurrent spillage up into the nozzle of the syringe. The needle is then removed from the tumor and, if there is still vacuum present, the syringe is detached from it. Air is then drawn up into the syringe, the needle is reattached, and the small amount of fluid with cells therein in the needle is forced out of the needle by operation of the syringe and blown onto a microscope slide. The amount of fluid, which is generally small, is then smeared against another slide to produce a film on both slides, and then the film is air dried and appropriately stained. Typically, an accurate analysis of the fluid can be made from a microscopic examination of these slides by an expert.

FIGS. 1A-1B illustrate a conventional fine needle aspiration device. In FIGS. 1A-1B, the stylet 20 tip is illustrated as being located inside the cannula tip 40. FIGS. 1A-1B also illustrate the cannula hub 60 that is molded to, glued to, or otherwise formed together with, the cannula 50, and the stylet hub 80 which is also molded to, glued to, or otherwise formed together with, the stylet. In operation, once both the stylet tip 20 and the cannula tip 40 are inserted adjacent to or in suspect regions of the body of the patient, the stylet tip 20 may be removed and a syringe may be provided in place of the stylet hub 80 to aspirate liquid or cellular samples into the cannula 50.

A Computerized Tomography (CT) gantry is a cylindrical device that is part of a CT scanner, houses the components necessary to produce and detect x-rays to create a CT image, and through which a patient may be placed in order to perform CT imaging of the body of the patient. The x-ray tube and detectors are positioned opposite each other and rotate around the gantry aperture. Utilizing CT imaging to determine a biopsy location and then confirm needle placement prior to biopsy is one method by which clinicians can verify the correct site has been biopsied via fine needle aspiration. However, the diameter of most gantries, generally barely allows patients to fit within them. As such, performing a task such as a fine needle aspiration biopsy, for example, presents difficulties due to the fact that typical biopsy devices do not fit within the restricted space between the patient's body and the inner diameter of a CT gantry.

There is a need in the art, therefore, for fine needle aspiration biopsy devices capable of being properly operated within the restricted space of a CT gantry.

SUMMARY OF THE INVENTION

In light of the above described problems and unmet needs, aspects of the current invention provide systems and devices for providing a fine needle aspiration biopsy device with a modified hub through which a vacuum is delivered to the targeted tissue for removal, the vacuum being provided via flexible tubing capable of fitting within a restricted space such as, for example, a CT gantry, and capable of extending along an axis other than a longitudinal axis of the biopsy device. For additional clarity, the longitudinal axis of the biopsy needle corresponds to the radial axis of the CT gantry. According to various aspects, the vacuum may draw the tissue into the needle. For example, the biopsy device may be manipulatable within a restricted space as provided by the modified hub and the flexible tubing that is located along an axis other than an axis of the biopsy device.

According to various aspects of the current invention, a vacuum source may be provided to provide suction during a fine needle aspiration procedure, the vacuum source being connected to a modified hub via flexible tubing that may be positioned along a direction other than the longitudinal or axial direction of the needle. When the needle is inserted in the body of a patient while the patient is located inside the restricted space of a CT gantry, the vacuum source may be positioned outside the CT gantry via the flexible tubing. The vacuum source may also be positioned on the patient so it can slide into the CT gantry with the patient.

Additional advantages and novel features of these aspects of the invention will be set forth in part in the description that follows, and in part will become more apparent to those skilled in the art upon examination of the following or upon learning by practice of the invention.

BRIEF DESCRIPTION OF THE DRAWINGS

Various example aspects of the systems and methods will be described in detail, with reference to the following figures, wherein:

FIGS. 1A-1B illustrate a conventional fine needle aspiration device;

DETAILED DESCRIPTION

These and other features and advantages of this invention are described in, or are apparent from, the following detailed description of various example aspects.

Figure 2A:
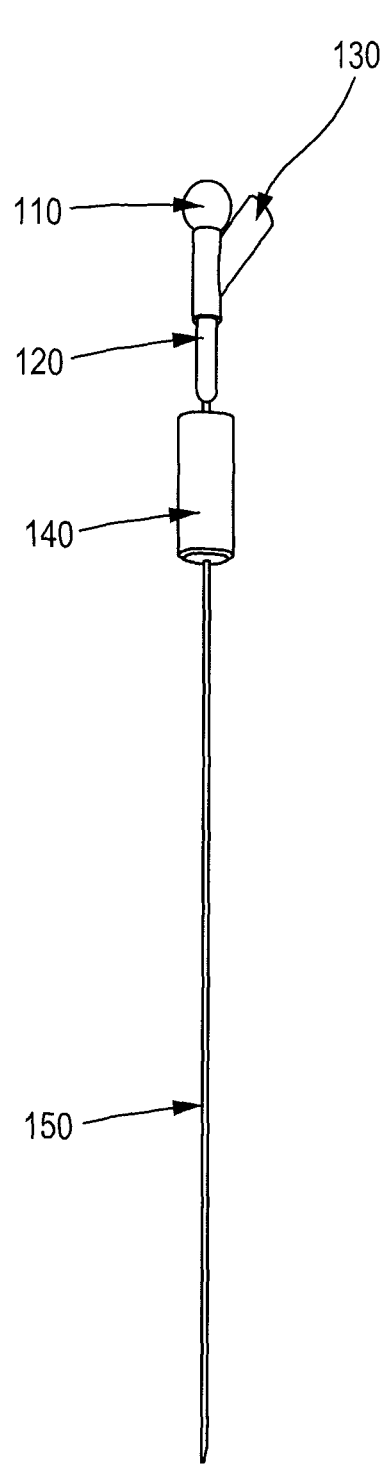
FIGS. 2A-2B illustrate a biopsy device according to various aspects of the current invention.
Figure 2B:
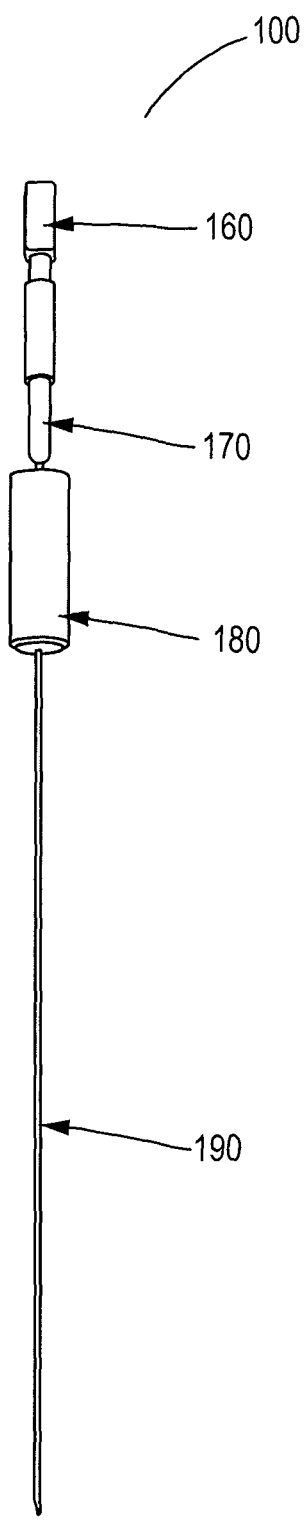

FIGS. 2A-2B illustrate a fine needle aspiration devices 100 and 102 according to various aspects of the current invention. According to various aspects, the fine needle aspiration device 102 in FIG. 2A includes a stylet port 110 into which a stylet with stylet hub (not shown) may be inserted during operation. According to various aspects, the stylet port 110 may be part of a hub 120, and in the case of vacuum-assisted operation, the hub 120 may include another port 130, which may be an angled port, to provide a path for vacuum to flow during operation. Accordingly, during a biopsy, the vacuum port 130 may be used to provide vacuum to the fine needle aspiration device 102 and facilitate the acquisition of liquid or cellular samples. It should be noted that the vacuum may be provided either after or before fine needle aspiration device 102 is inserted in the body of the patient. According to various aspects, the fine needle aspiration device 102 may also include a finger grip 140 that may be used by an operator to hold the fine needle aspiration device 102 and to, for example, perform manual oscillations of the cannula 150 within the target site and remove liquid or cellular samples from the body of a patient. For example, as the cannula 150 oscillates in and out of the body of the patient, a distal portion of the cannula 150 may collect several small liquid or cellular samples. Accordingly, the fine needle aspiration biopsy may be performed, as discussed below with respect to FIG. 3, by an operator oscillating the cannula 150 in and out of the body of the patient.

In operation, the cannula 150 and stylet (not shown) assembly may be inserted in the body of the patient, with the tips of the cannula 150 and stylet being used as an incision tip to penetrate the body of the patient. According to various aspects, once the cannula 150 and stylet are inserted in the body of the patient to the desired target site, the stylet may be removed from the cannula 150, and a vacuum source may be coupled to the cannula 150 via the port 130. If the hub includes two separate ports, such as port 110 for the stylet and port 130 for the vacuum line, then when the stylet is removed from the cannula 150, the port 110 may be plugged to avoid leakage of air when the vacuum is applied via the port 130. Port 110 may be plugged by including, for example, a septum within port 110 such that when the stylet is removed port 110 automatically seals itself. Alternatively, port 110 may be plugged by attaching, for example, a connector to plug the port. Accordingly, when a vacuum is applied to the cannula 150 via port 130, liquid or cellular samples may be transferred from inside the body of the patient to the cannula. While the vacuum is applied, the clinician may utilize finger grip 140 to oscillate device 102 in order to capture samples from more than one location within the targeted region. Once enough liquid and/or cellular samples have been collected, the vacuum may be turned off and the cannula 150 may be removed from the body of the patient for later analysis of the collected samples.

In FIG. 2B, the fine needle aspiration device 100 may include a stylet (not shown), which is attached to a stylet hub 160, the stylet being inserted through a cannula hub 170. In the example illustrated in FIG. 2B, the cannula hub 170 is a straight hub that does not include a vacuum port such as the port 130 of the hub 120 of FIG. 2A. However, as discussed with respect to FIG. 2A, once the cannula 190 and stylet are inserted in the body of the patient at the desired location, the stylet may be removed from the cannula 190 by disconnecting the stylet hub 160 from the cannula hub 190 and pulling the stylet out of the cannula 190, and a vacuum source may be coupled to the cannula 190 at the cannula hub 170. According to various aspects, the fine needle aspiration device 100 may include a finger grip 180 that may be used by an operator to hold the biopsy device 100.

In operation, the cannula 190 and stylet (not shown) assembly may be inserted in the body of the patient, with the tips of the cannula 190 and stylet being used as an incision tip to penetrate the body of the patient. According to various aspects, once the cannula 190 and stylet are inserted in the body of the patient to the targeted area, the stylet may be removed from the cannula 190, and a vacuum source may be coupled to the cannula 150 via the cannula hub 170. The vacuum source may not be coaxially aligned with cannula 150, as will be further described with reference to FIGS. 4A-4B. Accordingly, when a vacuum is applied to the cannula 190 via port 170, liquid or cellular samples may be transferred from inside the body of the patient to the cannula. While the vacuum is applied, the clinician may utilize finger grip 180 to oscillate device 100 in order to capture samples from more than one location within the targeted region. Once enough liquid and/or cellular samples have been collected, the vacuum may be turned off and the cannula 190 may be removed from the body of the patient for later analysis of the collected samples.

Because imaging equipment, processing and techniques have improved significantly over the last decade, the need for fine needle aspiration that improves the imaging of the needle with respect to the imaging modality is needed. One example of significant improvements in imaging is in the area of ultrasound. By adding grooves or rings to the outer surface of the fine needle aspiration cannula or adding texturing such as sand blasting to the outer surface, the needle will be significantly more visible under ultrasound. These improvements to visualization allow the clinician to better place the needle in close proximity to the tissue or fluid that is to be aspirated. The rings or texturing can also be positioned in a repeating pattern to provide visual indication of dimensions while visualizing under the specified image modality.

Figure 3:
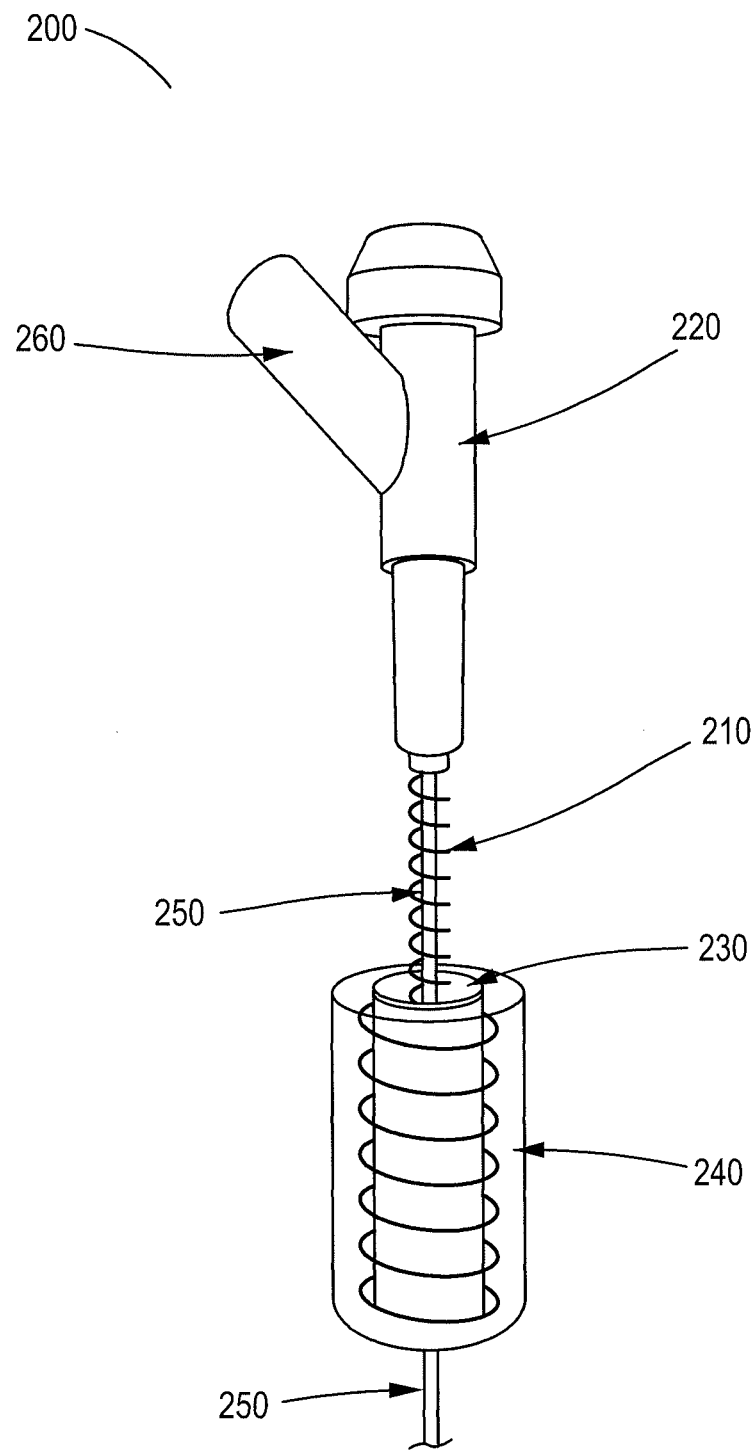
FIG. 3 illustrates a spring loaded attachment of a biopsy device according to various aspects of the current invention.

FIG. 3 illustrates a spring loaded attachment of a fine needle aspiration device 200 according to various aspects of the current invention. In FIG. 3, the fine needle aspiration device 200 includes a finger grip 240 that is provided around a housing 230 built around the cannula 250 of the fine needle aspiration device 200. Accordingly, an operator may hold the fine needle aspiration device 200 by the finger grip 240 without affecting the operation of the device 200, and manually locate the device 200 in the body of the patient so as to be near lesions of interest. According to various aspects, the hub 220, which may be coupled to the cannula 250 and possibly to a vacuum line via the vacuum port 260, may have a free floating spring 210 positioned inside the housing 230 and around the cannula 250. Accordingly, an operator may hold the finger grip 240 between two fingers and push the hub 220 towards the finger grip 240 with another finger. As a result, in the cannula 250 may be pushed forward in the same direction as the hub. The finger tip motion, as opposed to the reciprocating motions driven by the wrist in current biopsy devices, also provides better control of the biopsy process so as not to cause unintended damage to non-sampled tissue. When the biopsy device 200 is located inside the body of a patient, the cannula 250 may thus penetrate deeper into the body of the patient as a result of the movement of the hub 220 described above to sample relevant lesions in the body. As a result of the force pushing the spring towards the finger grip 240, the spring 210 may compress as the hub 220 is pushed towards the finger grip 240, and then may expand away from the finger grip 240, or backwards, upon relaxation of the pushing force. As a result of the resulting oscillation motion of the hub 220, and thus of the cannula 250, between a forward and a backward position, liquid and/or cellular samples may be collected via the oscillating movement of the cannula 250, which is aided by the vacuum applied through the cannula via vacuum port 260.

Figure 4B:
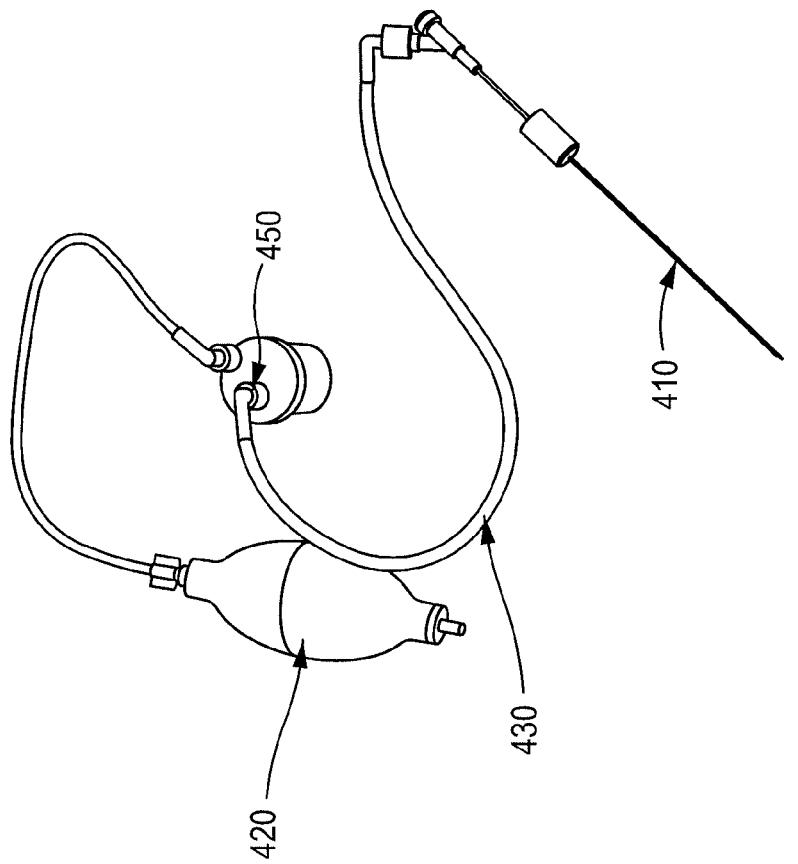
FIGS. 4A-4B illustrate a flexible tubing coupled to a vacuum-assisted biopsy device according to various aspects of the current invention.
Figure 4A:
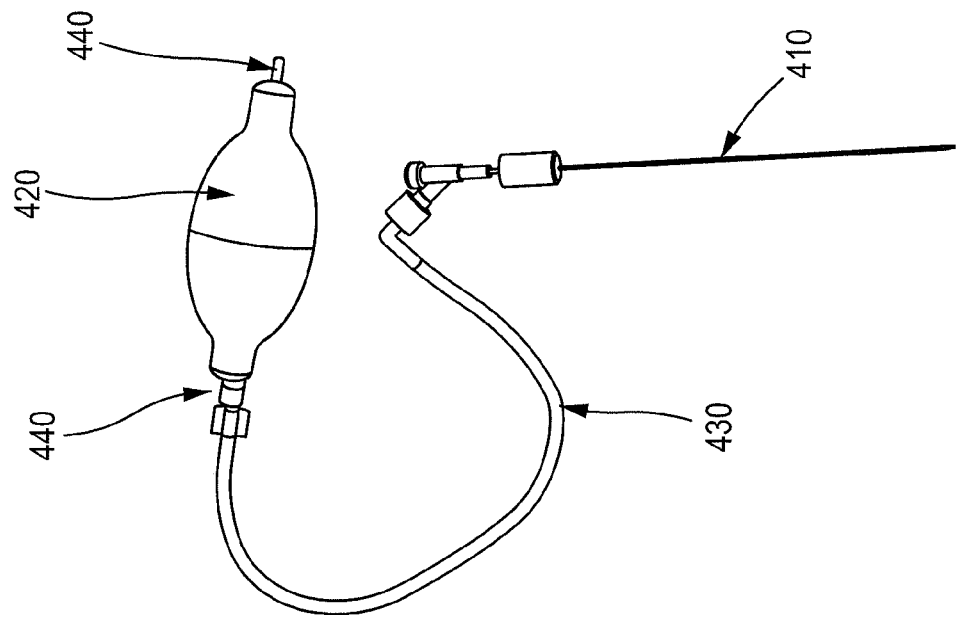

FIGS. 4A-4B illustrate several configurations of a flexible tubing coupled to a biopsy or fine needle aspiration device according to various aspects of the current invention. In FIGS.

4A-4B, a biopsy or fine needle aspiration device 410 may be coupled to a pump 420 via a length of flexible tubing 430. Fine needle aspiration device 410 may include a hub with two or more ports, as shown in the figure, but it may also include a hub with a single port (not shown). Various hub configurations have been previously described with reference to FIGS. 2A-2B. According to various aspects, a vacuum may be provided from the pump 420 to assist in the operation of the biopsy device by, for example, drawing liquid and/or cellular samples into the fine needle aspiration device 410 and permit the collection of the fluid and/or cellular samples from the body of a patient. According to various aspects, the vacuum provided via the pump 420 may be controlled via one or more one-way valves 440, as illustrated more specifically in FIG. 4A, the one or more one-way valves 440 ensuring that vacuum pump 420 only pulls material from the patient and no air is introduced inside the body of the patient during operation. According to other aspects of the current invention, a fluid collection chamber 450 may be provided along the path of the vacuum line in order to collect any fluid extracted from the body of the patient during biopsy, as illustrated more specifically in FIG. 4B, and also to prevent fluid from entering the pump 420. Although a manually operated pump 420 is illustrated in FIGS. 4A-4B, the ordinary person skilled in the art will understand that other vacuum creating devices such as, e.g., a syringe or a battery operated vacuum pump may also be utilized instead.

According to various aspects of the current invention, when a patient is undergoing a CT scan and a biopsy needs to be performed to remove liquid or cellular samples while the patient is positioned in the CT gantry, using the above-described biopsy or fine needle aspiration device would allow an operator to perform a biopsy in the restricted space between the body of the patient and the inside diameter of the CT gantry. According to various aspects, in operation, the biopsy or fine needle aspiration device 410 may be placed in proximity to the body of the patient inside the CT gantry, and the flexible tubing 430 may be extended from the biopsy device to the vacuum source 440, the vacuum source 440 being located outside the CT gantry, or upon the patient. Accordingly, performing a vacuum-assisted biopsy while taking a CT scan and while the patient is inside the CT gantry becomes possible, particularly when the space inside the CT gantry may not allow enough space for an operator to manually operate the biopsy device as discussed above with respect to FIG. 3.

In some instances, it is desirable to obtain larger amounts of tissue than can be obtained by traditional fine needle aspiration devices as described above, while still avoiding removing large cores of tissue that are typically removed in traditional biopsies utilizing a spring-loaded biopsy gun. In such instances, a slightly modified fine needle aspiration device may be used to capture cellular material, as described below with reference to FIGS. 5A-5B.

Figure 5A:
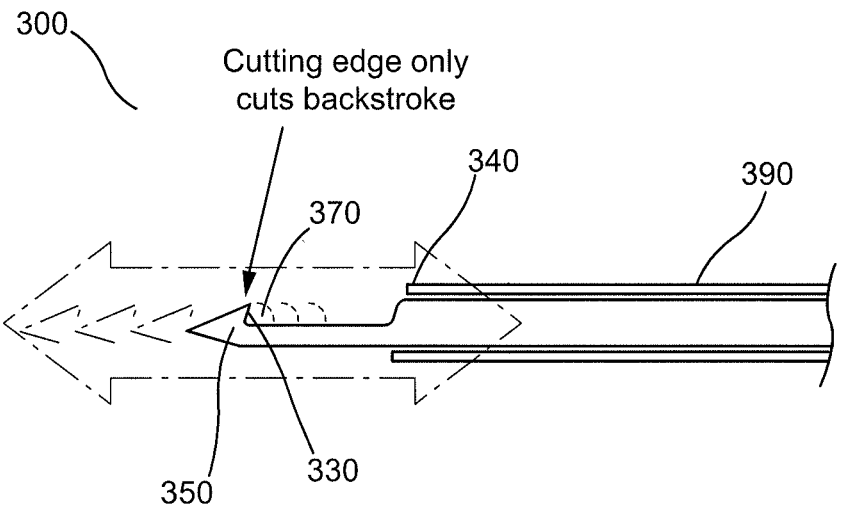
FIGS. 5A-5B illustrate a stylet and cannula in operation, according to various aspects of the current invention.
Figure 5B:
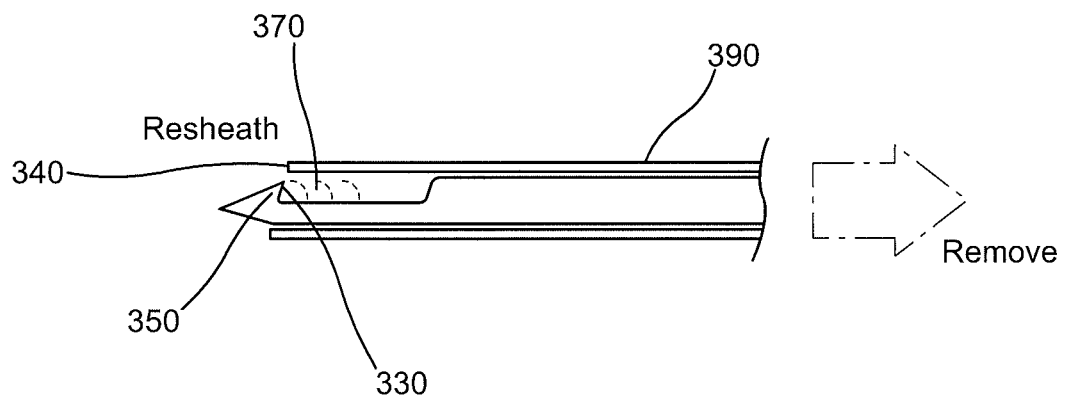

FIGS. 5A-5B illustrate a stylet and cannula in operation, according to various aspects of the current invention. In FIG. 5A, the stylet and cannula system 300 is illustrated in operation, where the stylet or needle 350 is extended and has partially or completely severed a tissue sample 370 such as, for example, a semi-liquid sample or a cellular sample. According to various aspects, when the stylet 350 is inserted inside the body of a patient, some tissue may become trapped in the notch of the stylet 350. As such, if removal of the tissue sample 370 is accomplished by pulling back the stylet 350, the edge 330 of the stylet 350 may act as a knife to cut the tissue sample 370 away from the rest of the body of the patient, and any remaining tissue may be further severed by the edge 340 of the cannula 390 when the stylet 350 is pulled back into the cannula 390. Additionally, stylet 350 may include a finger grip (not shown) similar to the finger grip described with reference to FIG. 3, such that the operator may manually oscillate the stylet relative to the cannula 390 in order to scrape cells from various locations within the targeted lesion. A vacuum source (not shown) similar to those previously described with reference to FIGS. 4A-4B may also be coupled to the stylet hub (not shown) in order to bias the tissue toward stylet 350, thus providing more tissue for sampling than would typically be available if a vacuum source was not used. Once the tissue sample 370 is severed from the body of the patient, the entire biopsy device 300, including the stylet 350 and the cannula 390, may be removed from the body of the patient, and the tissue sample 370 may be collected. Alternatively, stylet 350 may include a plurality of wire bristles instead of a notch. Using the oscillating motion described above would cause the bristles to scrape and retain small amounts of tissue and/or cells from the target site.

While aspects of this invention have been described in conjunction with the example features outlined above, various alternatives, modifications, variations, improvements, and/or substantial equivalents, whether known or that are or may be presently unforeseen, may become apparent to those having at least ordinary skill in the art. Accordingly, the example aspects of the invention, as set forth above, are intended to be illustrative, not limiting. Various changes may be made without departing from the spirit and thereof. Therefore, aspects of the invention are intended to embrace all known or later-developed alternatives, modifications, variations, improvements, and/or substantial equivalents.

What is claimed is:

1. A biopsy device comprising:
   a moveable hub coupled to a first end of a cannula and having a needle port and a vacuum port, the vacuum port being in communication with the cannula;
   a vacuum line in communication with the vacuum port;
   a stationary housing surrounding a portion of the cannula between the first end and an opposing second end, the stationary housing being distal to the hub and separated by a distance from the hub; and
   a biasing member coupled with the moveable hub and the stationary housing, the biasing member extending from the moveable hub to the stationary housing along the distance, and the biasing member imparting a biasing force on the hub in a direction away from the stationary housing,
   wherein an application of force on the hub sufficient to overcome the biasing force of the biasing member translates the moveable hub and the cannula in a direction toward the stationary housing, and
   wherein when the cannula is inserted in the body of the patient, a vacuum is provided via the vacuum line to aspirate liquid and cellular samples from the body of the patient into the cannula.

2. The biopsy device of claim 1, wherein
   the vacuum line includes a flexible tubing operable along a plurality of axes.

3. The biopsy device of claim 2,
   wherein the flexible tubing is operable in a confined space.

4. The biopsy device of claim 3,
   wherein the confined space includes a space inside a CT gantry.

5. The biopsy device of claim 1,
   wherein the vacuum port is coupled to a vacuum source via the vacuum line and a vacuum control device.

6. The biopsy device of claim 5,
wherein the vacuum control device includes a pump and at least one valve.

7. The biopsy device of claim 6,
wherein the at least one valve includes at least one one-way valve.

8. The biopsy device of claim 1,
further comprising a finger grip surrounding the stationary housing.

9. The biopsy device of claim 1, wherein the stationary housing is configured to be gripped by two fingers and wherein the moveable hub is configured to be actuated by a third finger.

10. The biopsy device of claim 1, wherein the stationary housing has a cylindrical shape.

11. A method of performing a biopsy using a fine needle aspiration device having a cannula having a first end and an opposing second end, a movable hub coupled to the first end of the cannula, a stationary housing surrounding a portion of the cannula between the first end and the second end, the stationary housing being distal to the hub and separated by a distance from the hub, and a biasing member coupled with the hub and the housing, the biasing member extending from the moveable hub to the stationary housing along the distance and imparting a biasing force on the hub in a direction away from the stationary housing, the method comprising:
   coupling the cannula to a vacuum source;
   inserting the cannula in the body of a patient;
   applying a vacuum to the cannula via the vacuum source;
   applying a force on the moveable hub in a direction toward the stationary housing sufficient to overcome the biasing force imparted by the biasing member, thereby translating the moveable hub and the cannula in the direction toward the stationary housing; and
   aspirating a liquid sample or a cellular sample into the cannula via the vacuum applied to the cannula.

12. The method of claim 11,
wherein the vacuum is applied one of before, during or after inserting the cannula in the body of the patient.

13. The method of claim 11,
wherein a stylet is provided in the cannula prior to inserting the cannula in the body of the patient to prevent clogging of the cannula.

14. The method of claim 13,
wherein the stylet is removed from the cannula prior to aspirating a liquid or cellular sample from the body of the patient.

15. The method of claim 11,
further comprising releasing the force on the moveable hub thereby allowing the biasing member to translate the moveable hub and the cannula in a direction away from the stationary housing.

16. The method of claim 15,
wherein the fine needle aspiration device further comprises a finger grip surrounding the stationary housing, and
wherein gripping the stationary housing comprises gripping the finger grip contemporaneously with releasing the force on the movable hub.

17. The method of claim 11,
wherein the fine needle aspiration device further comprises a finger grip surrounding the stationary housing, and
wherein gripping the stationary housing comprises gripping the finger grip contemporaneously with applying the force on the moveable hub.

18. The method of claim 11, wherein the stationary housing has a cylindrical shape.

\* \* \* \* \*